United States Patent [19]

van Daalen et al.

[11] 4,070,365
[45] Jan. 24, 1978

[54] PYRAZOLINE COMPOUNDS

[75] Inventors: Jan Johannes van Daalen, Weesp; Rudolf Mulder, Lunteren, both of Netherlands

[73] Assignee: U.S. Philips Corporation, New York, N.Y.

[21] Appl. No.: 594,205

[22] Filed: July 9, 1975

[30] Foreign Application Priority Data

July 12, 1974 Netherlands .......................... 7409433

[51] Int. Cl.$^2$ ...................... C07D 231/06; A01N 9/22
[52] U.S. Cl. ................................. 548/379; 424/273 P
[58] Field of Search ..................... 260/310 D; 424/273

[56] References Cited
FOREIGN PATENT DOCUMENTS 2,304,584  8/1973  Germany .............................. 260/310

Primary Examiner—Donald B. Moyer
Attorney, Agent, or Firm—Frank R. Trifari; Norman N. Spain

[57] ABSTRACT

The invention relates to new 1,3,4-substituted $\Delta^2$-pyrazolines having an insecticidal activity. The compounds are active in particular against larvae of insects such as larvae of colorado beetle, cabbage butterfly and yellow-fever mosquito. On the basis of their activity the compounds, after having been processed to the usual compositions, may be used in controlling insects, in particular in the field of agriculture and horticulture. The dosage is 0.05–1 kg of the active substance per hectare. A most active compound is the substance 1-(4-chlorophenylcarbamoyl)-3-(4-chlorophenyl)-4-phenyl$\Delta^2$-pyrazoline.

15 Claims, No Drawings

PYRAZOLINE COMPOUNDS

From German Offenlegungsschrift 2,304,584 in the name of Applicants it is known that pyrazoline compounds which have a substitute in the positions 1,3 or 1,3,5 of the pyrazoline ring exert a biocidal activity with respect to arthropoda, for example, mites and insects.

It has now been found that new pyrazoline compounds which correspond to the formula given below and which, as may be read from the formula, have a substituent in the positions 1,3 and 4 of the pyrazoline ring, have a very stronginsecticidal activity.

The compounds according to the present invention may be represented by the formula

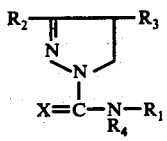

wherein $R_1$ is an alkyl group, a cycloalkyl group, a phenylalkyl group of which the phenyl nucleus may be substituted with halogen, alkyl or nitro, a heterocyclic ring which comprises 1-2 nitrogen atoms and may be substituted with halogen, alkyl or nitro, a phenyl group, a phenyl group which in the positions 2, 3 or 4 has 1-2 substituents chosen from the group consisting of halogen atom, alkyl group possibly substituted with halogen, a cycloalkyl group, an alkylthio group, an alkoxy group, a dialkylamino group, an alkylsulphonyl group, an acyl group, an acylamino group, a cyano group, a nitro group and a phenyl group which may be substituted with halogen, $R_2$ and $R_3$ are equal or different and have the meanings of an alkyl group, a cycloalkyl group, a pyridyl or thienyl group which may be substituted with halogen, alkyl or nitro, a phenyl group or a phenyl group substituted with 1-2 substituents selected from the group consisting of halogen atom, an alkyl group possibly substituted with halogen, a cycloalkyl group, an alkylthio group, an alkoxy group, a mono or dialkylamino group, a nitro group, a phenyl group possibly substituted with halogen, and a cyano group, $R_4$ is a hydrogen atom or an alkyl group having 1-15 carbon atoms and X is an oxygen atom or a sulphur atom.

If an alkyl group, a phenylalkyl group, an alkylthio group, an alkoxy group, an alkylamino group, a dialkylamino group, or an alkylsulphonyl group occurs in the substituents $R_1$, $R_2$ or $R_3$, then the alkyl radical present in such groups comprises 1-4 carbon atoms. A cycloalkyl group comprises 3-6 carbon atoms.

If an acyl group or an acylamino group occurs in $R_1$, then the acyl part of such a group is preferably derived from an aliphatic monocarbonic acid, for example, acetic acid or propionic acid.

When $R_1$ represents a heterocyclic ring containing 1-2 nitrogen atoms, then this is preferably a pyridine ring or a pyrimidine ring.

From the biological evaluation examination underlying the present invention it has been found that the compounds show a larvicidal activity and are capable even in small dosages to control, for example, larvae of beetles, larvae of mosquitoes as well as caterpillars. Moreover, the compounds show a good activity against adult stages of insects.

It has surprisingly been found that the insecticidal activity of the compounds according to the invention differs very significantly both quantitatively, that is activity level, and qualitatively, that is activity spectrum, from that of the known 1,3- and 1,3,5-substituted pyrazolines. It has been found more in particular that the average activity level of the group of compounds according to the invention is much higher than that of the group of known pyrazolines. It has furthermore been found that upon comparison of the activity of a substance according to the invention relative to a given insect with the corresponding activity of the isomeric compound from the series of known 1,3,5-substituted pyrazolines, the substance according to the invention generally shows a much higher activity level and also a wider activity spectrum. For example, it has been established that in some cases the insecticidal activ of a substance according to the invention as compared with that of the isomeric known compound shows a more than 700-fold increase. In general the insecticidal activity of the inventive substances is approximately 9–730 times stronger than that of the isomeric known pyrazolines. The wider activity spectrum of the substances according to the invention has been established in particular in experiments in which the compounds are tested for activity with respect to larvae of colorado beetle, of cabbage butterfly and of yellow-fever mosquito. It has been found that in many cases the inventive substances also have a good activity against the yellow-fever mosquito in addition to an excellent activity against both Colorado beetle and caterpillar. In the known isomeric compounds from the series of 1,3,5-substituted pyrazolines and 1,3-substituted compounds, often a less strong activity against caterpillar (larva of cabbage butterfly) is found in addition to a good activity against larvae of Colorado beetle and in many cases no or no noteworthy activity against the larvae of the yellow-fever mosquito to. It has furthermore been found that some of the compounds according to the invention show activity against Lucilia s.p.p., a veterinary parasite. Therefore, the compounds in question may also be processed to composition which may be used in veterinary medicine.

A strong insecticidal activity has been found in particular in compounds according to the invention which correspond to the formula

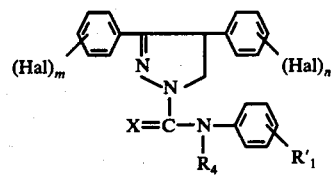

wherein Hal is a halogen atom, $R'_1$ is a hydrogen atom or a substituent present in the 3- or 4-position of the phenyl ring which is chosen from the group consisting of a halogen atom, an alkyl group having 1-4 carbon atoms which may be substituted with halogen, an alkylthio group having 1-4 carbon atoms, an alkoxy group having 1-4 carbon atoms, a cyano group and a nitro group or wherein $R'_1$ is a 3,4-dichloro group, X is an oxygen atom or a sulphur atom, $R_4$ has the above meanings, $m = 0$ or 1, and $n = 0$, 1 or 2.

Of this group of active substances the most active compounds can be represented by the formula

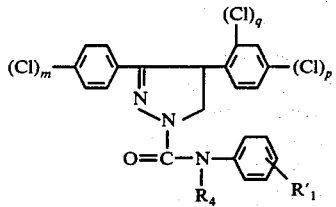

wherein $R'_1$ and $R_4$ have the above-described meanings, $m = 0$ or $1$, $p = 0$ or $1$, $q = 0$ or $1$.

This latter group of substances according to the invention includes compounds which even in a concentration of approximately 0.3–1 ppm cause a 90–100% mortality of Colorado beetle larvae. Such compounds may be represented by the formula

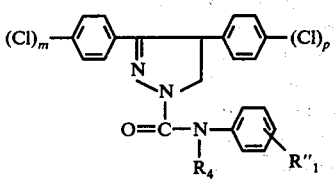

As most active substances according to the invention which, in a concentration of 0.3 – 1 ppm, show an optimum activity with respect to Colorado beetle larvae, in a concentration of 0.3 – 30 ppm show a maximum activity with respect to caterpillars, and in a concentration of 0.03–0.3 ppm show a maximum activity against larvae of yellow-fever mosquito may be mentioned:

1-(4-chlorophenylcarbamoyl) -3-(4-chlorophenyl)-4-phenyl-$\Delta^2$-pyrazoline. Melting point 177° C.

1-(4-chlorophenylcarbamoyl)-3,4-bis(4-chlorophenyl)-$\Delta^2$-pyrazoline. Melting point 162° C.

1-(4-bromophenylcarbamoyl)-3,-4-diphenyl-$\Delta^2$-pyrazoline. Melting point 170° C.

1-(4-chlorophenylcarbamoyl)-3,-4-diphenyl-$\Delta^2$-pyrazoline. Melting point 163° C. 1-(4-iodophenylcarbamoyl)-3,4-bis-(4-chlorophenyl) -$\Delta^2$-pyrazoline. Melting point 189° C.

1-(4-(fluorophenylcarbamoyl)-3,4-bis-(4-chlorophenyl) -$\Delta^2$-pyrazoline. Melting point 140° C.

1-(4-chlorophenylcarbamoyl)-3-phenyl-4-(4-chlorophenyl)-$\Delta^2$-pyrazoline. Melting point 137° C.

1-(3,4-dichlorophenylcarbamoyl)-3-phenyl-4-(4-chlorophenyl)-$\Delta^2$-pyrazoline. Melting point 170° C.

1-(4-methoxyphenylcarbamoyl)-3,4-bis-(4-chlorophenyl) -$\Delta^2$-pyrazoline. Melting point 158° C.

1-(3-nitrophenylcarbamoyl)-3,4-bis-(4-chlorophenyl) -$\Delta^2$-pyrazoline. Melting point 165° C.

1-[N-(4-chlorophenyl)-N-methyl]-carbamoyl-3-(4-chlorophenyl)-4-phenyl-$\Delta^2$-pyrazoline. Melting point 142° C.

1-[N-(4-chlorophenyl)-N-ethyl]-carbamoyl-3-(4-chlorophenyl)-4-phenyl-$\Delta^2$-pyrazoline. Oil.

1-[N-n.butyl-N-(4-chlorophenyl)]-carbamoyl-3-(4-chlorophenyl)-4-phenyl-$\Delta^2$-pyrazoline. Oil.

1-[N-(4-chlorophenyl)-N-n.octyl]-carbamoyl-3-(4-chlorophenyl)-4-phenyl-$\Delta^2$-pyrazoline. Oil.

1-[N-(4-chlorophenyl)-N-n.dodecyl]-carbamoyl-3-(4-chlorophenyl)-4-phenyl-$\Delta^2$ -pyrazoline. Oil.

Examples of other active substances according to the invention are:

1-(4-methoxyphenyl carbamoyl)-3,4-diphenyl-$\Delta^2$-pyrazoline. Melting point 165° C.

1-(4-t.butylphenyl carbamoyl)-3,4-diphenyl-$\Delta^2$-pyrazoline. Melting point 189° C.

1-(4-n.butylphenylcarbamoyl)-3,4-diphenyl-$\Delta^2$-pyrazoline. Melting point 170° C.

1-(4-ethylphenylcarbamoyl)-3,4-diphenyl-$\Delta^2$-pyrazoline. Melting point 154° C.

1-phenylcarbamoyl-3,4-diphenyl-$\Delta^2$-pyrazoline. Melting point 185° C.

1-(4-nitrophenylcarbamoyl)-3,4-diphenyl-$\Delta^2$-pyrazoline. Melting point 190° C.

1-(phenylcarbamoyl)-3-(4-chlorophenyl)-4-phenyl-$\Delta^2$-pyrazoline. Melting point 157° C.

1-(4-methylthiophenylcarbamoyl)-3,4-bis(4-chlorophenyl)-$\Delta^2$-pyrazoline. Melting point 159° C.

1-(4-t.butylphenylcarbamoyl)-3,4-bis-(4-chlorophenyl)-$\Delta^2$-pyrazoline. Melting point 186° C.

1-(4-phenylphenylcarbamoyl)-3,4-bis-(4-chlorophenyl)-$\Delta^2$-pyrazoline. Melting point 162° C.

1-(4-methylphenylcarbamoyl)-3,4-bis-(4-chlorophenyl)-$\Delta^2$-pyrazoline. Melting point 195° C.

1-(o-tolylcarbamoyl)-3,4-bis-(4-chlorophenyl)-$\Delta^2$-pyrazoline. Melting point 186° C.

1-phenylcarbamoyl-3,4-bis-(4-chlorophenyl)-$\Delta^2$-pyrazoline. Melting point 141° C.

1-(4-bromophenylcarbamoyl)-3,4-bis-(4-chlorophenyl)$\Delta^2$-pyrazoline. Melting point 174° C.

1-(3-chlorophenylcarbamoyl)3,4-(bis-chlorophenyl)-$\Delta^2$-pyrazoline. Melting point 158° C.

1-(3-trifluoromethylphenylcarbamoyl)-3,4-bis-(4-chlorophenyl)-$\Delta^2$-pyrazoline. Melting point 147° C.

1-(3,4-dichlorophenylcarbamoyl)-3,4-bis-(4-chlorophenyl)-$\Delta^2$-pyrazoline. Melting point 216° C.

1-(4-nitrophenylcarbamoyl)-3,4-bis-(4-chlorophenyl)-$\Delta^2$-pyrazoline. Melting point 204° C.

1-(4-methoxyphenylcarbamoyl)-3-phenyl-4(4-chlorophenyl)-$\Delta^2$-pyrazoline. Melting point 151° C.

1-(4-ethylphenylcarbamoyl)-3-phenyl-4-(4-chlorophenyl)-$\Delta^2$-pyrazoline. Melting point 140° C.

1-(phenylcarbamoyl-3-phenyl-4-(4-chlorophenyl)-$\Delta^2$-pyrazoline. Melting point 224° C.

1-(4-methoxyphenylcarbamoyl)-3-(4-chlorophenyl)-4-(2,4-dichlorophenyl)-$\Delta^2$-pyrazoline. Melting point 165° C.

1-(4-n.butylphenylcarbamoyl)-3-(4-chlorophenyl)-4-(2,4-dichlorophenyl)-$\Delta^2$-pyrazoline. Melting point 132° C.

1-(p-tolylcarbamoyl)-3-(4-chlorophenyl)-4-(2,4-dichlorophenyl)-$\Delta^2$-pyrazoline. Melting point 136° C.

1-phenylcarbamoyl-3-(4-chlorophenyl)-4-(2,4-dichlorophenyl)-$\Delta^2$-pyrazoline. Melting point 157° C.

1-(4-chlorophenylcarbamoyl)-3-(4-chlorophenyl)-4-(2,4-dichlorophenyl)-$\Delta^2$-pyrazoline. Melting point 173° C.

1-(4-fluorophenylcarbamoyl)-3-(4-chlorophenyl)-4-(2,4-dichlorophenyl)-$\Delta^2$-pyrazoline. Melting point 157° C.

1-(3,4-dichlorophenylcarbamoyl)-3-(4-chlorphenyl)-4-(2,4-dichlorophenyl)-$\Delta^2$-pyrazoline. Melting point 172° C.

1-benzylcarbamoyl-3,4-bis-(4-chlorophenyl)-$\Delta^2$-pyrazoline. Melting point 97° C.

1-phenylthiocarbamoyl-3,4-diphenyl-$\Delta^2$-pyrazoline. Melting point 178° C.

1-phenylthiocarbamoyl-3,4-bis-(4-chlorophenyl)-$\Delta^2$-pyrazoline. Melting point 160° C.

1-(4-chlorophenylcarbamoyl)-3-(4-phenylphenyl)-4-(4-chlorophenyl)-$\Delta^2$-pyrazoline. Melting point 197° C.

1-(4-dimethylaminophenylcarbamoyl)-3-(4-phenylphenyl)-4-(4-chlorophenyl)-$\Delta^2$-pyrazoline. Melting point 179° C.

1-(4-n.butylsulphonylphenylcarbamoyl)-3-(4-phenylphenyl)-4-(4-chlorphenyl)-$\Delta^2$-pyrazoline. Melting point 130° C.

1-(4-ethylphenylcarbamoyl)-3-(4-phenylphenyl)-4-(4-chlorophenyl)-$\Delta^2$-pyrazoline. Oil.

1-(4-bromophenylcarbamoyl)-3-(4-phenylphenyl)-4-(4-chlorophenyl)-$\Delta^2$-pyrazoline. Melting point 199° C.

1-phenylcarbamoyl-3-(4-phenylphenyl)-4-(4-chlorophenyl)-$\Delta^2$-pyrazoline. Melting point 154° C.

1-(4-chlorophenylcarbamoyl)-3-(4-methoxyphenyl)-4-(4-chlorophenyl)-$\Delta^2$-pyrazoline. Melting point 155° C.

1-(4-t.butylphenylcarbamoyl)-3-(4-methoxyphenyl)-4-(4-chlorophenyl)-$\Delta^2$-pyrazoline. Melting point 139° C.

1-(4-dimethylaminophenylcarbamoyl)-3-(4-methoxyphenyl)-4-(4-chlorophenyl)-$\Delta^2$-pyrazoline. Melting point 168° C.

1-(4-isopropoxyphenylcarbamoyl)-3-(4-methoxyphenyl)-4-(4-chlorophenyl)-$\Delta^2$-pyrazoline. Melting point 169° C.

1-(4-nitrophenylcarbamoyl)-3-(4-methoxyphenyl)-4-(4-chlorophenyl)-$\Delta^2$-pyrazoline. Melting point 176° C.

1-(3-trifluoromethylphenylcarbamoyl)-3-(4-methoxyphenyl)-4-(4-chlorophenyl)-$\Delta^2$-pyrazoline. Melting point 164° C.

1-(4-chlorophenylcarbamoyl)-3-(4-nitrophenyl)-4-phenyl-$\Delta^2$-pyrazoline. Melting point 201° C.

1-(4-chlorophenylcarbamoyl)-3-p-tolyl-4-(4-chlorophenyl)-$\Delta^2$-pyrazoline. Melting point 166° C.

1-(4-isopropylphenylcarbamoyl)-3-p-tolyl-4-(4-chlorophenyl)-$\Delta^2$-pyrazoline. Melting point 184° C.

1-(4-isopropoxyphenylcarbamoyl)-3-p-tolyl-4-(4-chlorophenyl)-$\Delta^2$-pyrazoline. Melting point 151° C.

1-(3-trifluoromethylphenylcarbamoyl)-3-p-tolyl-4-(4-chlorophenyl)-$\Delta^2$-pyrazoline. Melting point 186° C.

1-(4-n.propylphenylcarbamoyl)-3-p-tolyl-4-(4-chlorophenyl)-$\Delta^2$-pyrazoline. Melting point 185° C.

1-(4-chlorophenylcarbamoyl)-3-(4-t.butylphenyl)-4-(4-chlorophenyl)-$\Delta^2$-pyrazoline. Melting point 173° C.

1-phenylcarbamoyl-3-(4-t.butylphenyl)-4-(4-chlorophenyl)-$\Delta^2$-pyrazoline. Melting point 139° C.

1-(4-ethoxyphenylcarbamoyl)-3-(4-t.butylphenyl)-4-(4-chlorophenyl)-$\Delta^2$-pyrazoline. Melting point 138° C.

1-(4-n.butylsulphonylphenylcarbamoyl)-3-(4-t.butylphenyl)-4-(4-chlorophenyl)-$\Delta^2$-pyrazoline. Melting point 205° C.

1-(3-trifluoromethylphenylcarbamoyl)-3-(4-t.butylphenyl)-4-(4-chlorophenyl)-$\Delta^2$-pyrazoline. Melting point 165° C.

1-(4-chlorophenylcarbamoyl)-3-(4-chlorophenyl)-4-n.butyl-$\Delta^2$-pyrazoline. Melting point 145° C.

1-(4-ethoxyphenylcarbamoyl)-3-(4-chlorophenyl)-4-n.butyl-$\Delta^2$-pyrazoline. Melting point 132° C.

1-(3-nitro-4-methoxyphenylcarbamoyl)-3-(4-chlorophenyl)-4-n.butyl-$\Delta^2$-pyrazoline. Melting point 140° C.

1-(4-nitrophenylcarbamoyl)-3-(4-chlorophenyl)-4-n.butyl-$\Delta^2$-pyrazoline. Melting point 150° C.

1-(4-phenylphenylcarbamoyl)-3-(4-chlorophenyl)-4-n.butyl-$\Delta^2$-pyrazoline. Melting point 170° C.

1-(4-ethylsulphonylphenylcarbamoyl)-3-(4-chlorophenyl)-4-n.butyl-$\Delta^2$-pyrazoline. Melting point 191° C.

1-(4-methylthiophenylcarbamoyl)-4-(4-chlorophenyl)-4-n.butyl-$\Delta^2$-pyrazoline. Melting point 154° C.

1-(2-chlorophenylcarbamoyl)-3,4-bis-(4-chlorophenyl)-$\Delta^2$-pyrazoline. Melting point 202° C.

1-(4-acetylphenylcarbamoyl)-3,4-bis-(4-chlorophenyl)-$\Delta^2$-pyrazoline. Melting point 208° C.

1-(4-ethylphenylcarbamoyl)-3,4-bis-(4-chlorophenyl)-$\Delta^2$-pyrazoline. Melting point 171° C.

1-(3-chloro-4-methylphenylcarbamoyl)-3,4-bis-(4-chlorophenyl)-$\Delta^2$-pyrazoline. Melting point 194° C.

1-(4-n.butylsulphonylphenylcarbamoyl)-3,4-bis-(4-chlorophenyl)-$\Delta^2$-pyrazoline. Melting point 190° C.

1-(4-ethylsulphonylphenylcarbamoyl)-3,4-bis-(4-chlorophenyl)-$\Delta^2$-pyrazoline. Melting point 196° C.

1-(4-methylsulphonylphenylcarbamoyl)-3,4-bis-(4-chlorophenyl)-$\Delta^2$-pyrazoline. Melting point > 240° C.

1-(4-isopropoxyphenylcarbamoyl)-3,4-bis-(4-chlorophenyl)-$\Delta^2$-pyrazoline. Melting point 164° C.

1-(4-dimethylaminophenylcarbamoyl)-3,4-bis-(4-chlorophenyl)-$\Delta^2$-pyrazoline. Melting point 213° C.

1-(3-chloro-4-methoxyphenylcarbamoyl)-3,4-bis-4-(4-chlorophenyl)-$\Delta^2$-pyrazoline. Melting point 188° C.

1-(2,4-dichlorophenylcarbamoyl)-3,4-bis-(4-chlorophenyl)-$\Delta^2$-pyrazoline. Melting point 229° C.

1-(4-n.butylphenylcarbamoyl)-3,4-bis-(4-chlorophenyl)-$\Delta^2$-pyrazoline. Melting point 131° C.

1-(4-isopropylphenylcarbamoyl)-3,4-bis-(4-chlorophenyl)-$\Delta^2$-pyrazoline. Melting point 172° C.

1-(4-ethoxyphenylcarbamoyl)-3,4-bis-(4-chlorophenyl)-$\Delta^2$-pyrazoline. Melting point 173° C.

1-(4-trifluoromethylphenylcarbamoyl)-3,4-bis-(4-chlorophenyl)-$\Delta^2$-pyrazoline. Melting point 149° C.

1-(3-nitro-4-methoxyphenylcarbamoyl)-3,4-bis-(4-chlorophenyl)-$\Delta^2$-pyrazoline. Melting point 214° C.

1-(4-isobutylphenylcarbamoyl)-3,4-bis-(4-chlorophenyl)-$\Delta^2$-pyrazoline. Melting point 169° C.

1-(4-cyanophenylcarbamoyl)-3,4-bis-(4-chlorophenyl)-$\Delta^2$-pyrazoline. Melting point 218° C.

1- -pyridylcarbamoyl-3,4-bis-(4-chlorophenyl)-$\Delta^2$-pyrazoline. Melting point 228° C.

1-methylcarbamoyl-3,4-bis-(4-chlorophenyl)-$\Delta^2$-pyrazoline. Oil.

1-n.butylcarbamoul-3,4-bis-(4-chlorophenyl)-$\Delta^2$-pyrazoline. Oil.

1-cyclohexylcarbamoyl-3,4-bis-(4-chlorophenyl)-$\Delta^2$-pyrazoline. Melting point 185° C.

1-isopropylcarbamoyl-3,4-bis-(4-chlorophenyl)-Δ²-pyrazoline. Melting point 144° C.
1-(4-chlorobenzylcarbamoyl)-3,4-bis-(4-chlorophenyl)-Δ²-pyrazoline. Melting point 160° C.
1-(4-chlorophenylthiocarbamoyl)-3,4-bis-(4-chlorophenyl)-Δ²-pyrazoline. Melting point 143° C.
1-(3-nitrophenylcarbamoyl) -3-(4-chlorophenyl)-4-phenyl-Δ²-pyrazoline. Melting point 192° C.
1-(4-phenylphenylcarbamoyl)-3-(4-chlorophenyl)-4-phenyl-Δ²-pyrazoline. Melting point 165° C.
1-(4-bromophenylcarbamoyl)-3-(4-chlorophenyl)-4-phenyl-Δ²-pyrazoline. Melting point 181° C.
1-(4-dimethylaminophenylcarbamoyl)-3-(4-chlorophenyl)-4-phenyl-Δ²-pyrazoline. Melting point 177° C.
1-(4-t.butylphenylcarbamoyl)-3-(4-chlorophenyl)-4-phenyl-Δ²-pyrazoline. Melting point 182° C.
1-(4-n.butylphenylcarbamoyl)-3-(4-chlorophenyl)-4-phenyl-Δ²-pyrazoline. Melting point 169° C.
1-(4-ethylphenylcarbamoyl)-3-(4-chlorophenyl)-4-phenyl-Δ²-pyrazoline. Melting point 156° C.
1-(3-trifluoromethylphenylcarbamoyl)-3-(4-chlorophenyl)-4-phenyl-Δ²-pyrazoline. Melting point 149° C.
1-(4-isopropoxyphenylcarbamoyl)-3-(4-clorophenyl)-4-phenyl-Δ²-pyrazoline. Melting point 138° C.
1-(4-trifluoromethylphenylcarbamoyl)-3-(4-chlorophenyl)-4-phenyl-Δ²-pyrazoline. Melting point 174° C.
1-(3-chlorophenylcarbamoyl)-3-(4-chlorophenyl)-4-phenyl-Δ²-pyrazoline. Melting point 155° C.
1-(4-nitrophenylcarbamoyl)-3-(4-chlorophenyl)-4-phenyl-Δ²-pyrazoline. Melting point 230° C.
1-(p-tolylcarbamoyl)-3-(4-chlorophenyl)-4-phenyl-Δ²-pyrazoline. Melting point 147° C.
1-(2-chlorophenylcarbamoyl)-3-(4-chlorophenyl)-4-phenyl-Δ²-pyrazoline. Melting point 193° C.
1-(4-fluorophenylcarbamoyl)-3-(4-chlorophenyl)-4-phenyl-Δ²-pyrazoline. Melting point 162° C.
1-(4-isobutylphenylcarbamoyl)-3-(4-chlorophenyl)-4-phenyl-Δ²-pyrazoline. Melting point 180° C.
1-(4-ethylsulphonylphenylcarbamoyl)-3-(4-chlorophenyl)-4-(phenyl)-Δ²-pyrazoline. Melting point 226° C.
1-(4-n.butylsulphonylphenylcarbamoyl)-3-(4-chlorophenyl)-4-phenyl-Δ²-pyrazoline. Melting point 179° C.
1-(4-methylthiophenylcarbamoyl)-3-(4-chlorophenyl)-4-phenyl-Δ²-pyrazoline. Melting point 165° C.
1-(4-cyanophenylcarbamoyl)-3-(4-chlorophenyl)-4-phenyl-Δ²-pyrazoline. Melting point 199° C.
1-(3-chloro-4-methylphenylcarbamoyl)-3-(4-chlorophenyl)-4-phenyl-Δ²-pyrazoline. Melting point 178° C.
1-(3-nitro-4-methoxyphenylcarbamoyl)-3-(4-chlorophenyl)-4-phenyl-Δ²-pyrazoline. Melting point 194° C.
1-(3,4-dichlorophenylcarbamoyl)-3-(4-chlorophenyl)-4-phenyl-Δ²-pyrazoline. Melting point 175° C.
1-(2,4-dichlorophenylcarbamoyl)-3-(4-chlorophenyl)-4-phenyl-Δ²-pyrazoline. Melting point 204° C.
1-(4-chlorobenzylcarbamoyl)-3-(4-chlorophenyl)-4-phenyl-Δ²-pyrazoline. Melting point 179° C.
1-methylcarbamoyl-3-(4-chlorophenyl)-4-phenyl-Δ²-pyrazoline. Melting point 135° C.
1-cyclohexylcarbamoyl-3-(4-chlorophenyl)-4-phenyl-Δ²-pyrazoline. Melting point 151° C.
1-pyridylcarbamoyl-3-(4-chlorophenyl)-4-phenyl-Δ²-pyrazoline. Melting point 224° C.
1-(4-chlorophenylthiocarbamoyl)-3-(4-chlorophenyl)-4-phenyl-Δ²-pyrazoline. Melting point 194° C.
1-(4-chlorophenylcarbamoyl)-3-(4-chlorophenyl)-4-methyl-Δ²-pyrazoline. Melting point 139° C.
1-(3,4-dichlorophenylcarbamoyl)-3-(4-chlorophenyl)-4-methyl-Δ²-pyrazoline. Melting point 160° C.
1-(3-nitro-4-methoxyphenylcarbamoyl)-3-(4-chlorophenyl)-4-methyl-Δ²-pyrazoline. Melting point 193° C.
1-(3-chloro-4-methoxyphenylcarbamoyl)-3-(4-chlorophenyl)-4-methyl-Δ²-pyrazoline. Melting point 145° C.
1-(4-n.butylphenylcarbamoyl)-3-(4-chlorophenyl)-4-methyl-Δ²-pyrazoline. Melting point 117° C.
1-(4-chlorophenylcarbamoyl)-3-(4-dimethylaminophenyl)-4-(4-chlorophenyl)-Δ²-pyrazoline. Melting point 205° C.
1-(4-ethylphenylcarbamoyl)-3-(4-dimethylaminophenyl)-4-(4-chlorophenyl-Δ²-pyrazoline. Melting point 148° C.
1-(4-ethylsulphonylphenylcarbamoyl)-3-(4-dimethylaminophenyl)-4-(4-chlorophenyl)-Δ²-pyrazoline. Melting point 130° C.
1-benzylcarbamoyl-3-(4-dimethylaminophenyl)-4-(4-chlorophenyl)-Δ²-pyrazoline. Melting point 143° C.
1-n.butylcarbamoyl-3-(4-dimethylaminophenyl)-4-(4-chlorophenyl)-Δ²-pyrazoline. Melting point 107° C.
1-(4-chlorophenylcarbamoyl)-3-(4-chlorophenyl)-4-(4-dimethylaminophenyl)-Δ²-pyrazoline. Melting point 190° C.
1-(4-ethylphenylcarbamoyl)-3-(4-chlorophenyl)-4-(4-dimethylaminophenyl)-Δ²-pyrazoline. Melting point 100° C.
1-(4-ethylsulphonylphenylcarbamoyl)-3-(4-chlorophenyl)-(4-dimethylaminophenyl)-Δ²-pyrazoline. Melting point 156° C.
1-(4-chlorophenylcarbamoyl)-3-(4-isopropoxyphenyl)-4-phenyl-Δ²-pyrazoline. Melting point 141° C.
1-(4-ethylphenylcarbamoyl)-3-(4-isopropoxyphenyl)-4-phenyl-Δ²-pyrazoline. Melting point 95° C.
1-(2,4-dichlorophenylcarbamoyl)-3,4-diphenyl-Δ²-pyrazoline. Melting point 167° C
1-(2,4-dichlorophenylcarbamoyl)-3-(4-chlorophenyl)-4-phenyl-Δ²-pyrazoline. Melting point 201° C.
1-(3,5-dichlorophenylcarbamoyl)-3-(4-chlorophenyl)-4-(4-chlorophenyl)-Δ²-pyrazoline. Melting point 214° C
1-(4-dimethylaminophenylthiocarbamoyl)-3-(4-chlorophenyl)-4-phenyl-Δ²-pyrazoline. Melting point 203° C
1-(3,5-dichlorophenylcarbamoyl)-3-(4-chlorophenyl)-4-phenyl-Δ²-pyrazoline. Melting point 234° C.
1-(4-methoxycarbamoylphenylthiocarbamoyl)-3-(4-chlorophenyl)-4-(4-chlorophenyl)-Δ²-pyrazoline. Melting point 205° C 1-(4-chlorophenylcarbamoyl)-3-(3,4-dimethoxyphenyl)-4-(4-chlorophenyl)-Δ²-pyrazoline. Melting point 182° C 1-(4-ethoxyphenylcarbamoyl)-3-(3,4-dimethoxyphenyl)-4-(4-chlorophenyl)-Δ²-pyrazoline. Melting point 161° C 1-(3-trifluoromethylphenylcarbamoyl)-3-(3,4-dimethoxyphenyl)-4-(4-chlorophenyl)-Δ²-pyrazoline. Melting point 180° C 1-(4-ethylphenylcarbamoyl)-3-(3,4-dimethoxyphenyl)-4-(4-chlorophenyl)-Δ²-pyrazoline. Melting point 167° C 1-(4-isopropylphenylcarbamoyl)-3-(3,4-dimethoxyphenyl)-4-(4-chlorophenyl)-Δ²-pyrazoline. Melting point 158° - 159° C 1-(3-chloro-4-methylphenylcarbamoyl)-3-(3,4-dimethoxyphenyl)-4-(4-chlorophenyl)-Δ²-pyrazoline. Melting point 159° C 1-(4-phenylphenylcarbamoyl)-3-(3,4-dimethoxyphenyl)-4-(4-chlorophenyl)-Δ²-pyrazoline. Melting point 212° C 1-[N-(4-chlorophenyl)-N-methylcarbamoyl]-3-(4-chlorophenyl)-4-(4-chlorophenyl)-Δ²-pyrazoline. Melting point 64° C (very active compound)

1-[4-(4-chlorophenyl)-phenylcarbamoyl]-3-(4-chlorophenyl)-4-(4-chlorophenyl)-Δ²-pyrazoline. Melting point 144° C 1-(p-ethoxyphenylthiocarbamoyl)-3-(4-chlorophenyl)-4-phenyl-Δ²-pyrazoline. Melting point 195° C 1-(4-chlorophenylcarbamoyl)-3-(4-bromophenyl)-4-phenyl-Δ²-pyrazoline. Melting point 178° C (very act.comp.)

1-(4-bromophenylcarbamoyl)-3-(4-bromophenyl)-4-phenyl-Δ²-pyrazoline. Melting point 184° C (very act.comp.)

1-(4-isopropoxyphenylcarbamoyl)-3-(4-bromophenyl)-4-(phenyl-Δ²-pyrazoline. Melting point 170° C (very act.comp.)

1-(4-isobutylphenylcarbamoyl)-3-(4-bromophenyl)-4-phenyl-Δ²-pyrazoline. Melting point 173° C 1-cyclohexylcarbamoyl-3-(4-bromophenyl)-4-phenyl-Δ²-pyrazoline. Melting point 153° C 1-(4-methylthiophenylcarbamoyl)-3-(4-bromophenyl)-4-phenyl-Δ²-pyrazoline. Melting point 168° C 1-[4-chlorophenyl)-phenylcarbamoyl]-3-(4-chlorophenyl-4-phenyl-Δ²-pyrazoline. Melting point 187° C 1-(4-acetylphenylcarbamoyl)-3-(4-chlorophenyl)-4-phenyl-Δ²-pyrazoline. Melting point 210° C 1-(4-chlorophenylcarbamoyl)-3-(4-bromophenyl)-4-(4-chlorophenyl)-Δ²-pyrazoline. Melting point 175° C (act.comp.)

1-(3-trifluoromethylphenylcarbamoyl)-3-(4-bromophenyl)-4-(4-chlorophenyl)-Δ²-pyrazoline. Melting point 130°-135° C.

1-(4-chlorophenylcarbamoyl)-3-(4-methylphenyl)-4-phenyl-Δ²-pyrazoline. Melting point 164° C 1-(4-methylphenylcarbamoyl)-3-(4-methylphenyl)-4-phenyl-Δ²-pyrazoline. Melting point 185°-186° C 1-(4-n.propylphenylcarbamoyl)-3-(4-methylphenyl)-4-phenyl-Δ²-pyrazoline. Melting point 159°-160° C 1-(4-ethoxyphenylcarbamoyl)-3-(4-methylphenyl)-4-phenyl-Δ²-pyrazoline. Melting point 164°-165° C 1-phenylcarbamoyl-3-(4-methylphenyl)-4-phenyl-Δ²-pyrazoline. Melting point 168°-169° C 1-(4-chlorophenylcarbamoyl)-3-(4-isopropylphenyl)-4-phenyl-Δ²-pyrazoline. Melting point 168°-170° C 1-(4-ethoxyphenylcarbamoyl)-3-(4-isopropylphenyl)-4-phenyl-Δ²-pyrazoline. Melting point 156°-158° C 1-(3-nitrophenylcarbamoyl)-3-(4-isopropylphenyl)-4-(phenyl-Δ²-pyrazoline. Melting point 160°-164° C 1-(4-methoxyphenylcarbamoyl)-3-(4-chlorophenyl)-4-phenyl-Δ²-pyrazoline. Melting point 164°-166° C 1-phenylcarbamoyl-3-(4-chlorophenyl)-4-(4-nitrophenyl)-Δ²-pyrazoline. Melting point 192° C 1-(4-ethylphenylcarbamoyl)-3-(4-chlorophenyl)-4-(4-nitrophenyl)-Δ²-pyrazoline. Melting point 150° C 1-(3-trifluoromethylphenylcarbamoyl)-3-(4-chlorophenyl)-4-(4-nitrophenyl)-Δ²-pyrazoline. Melting point 189°-192° C 1-(4-cyanophenylcarbamoyl)-3-(4-chlorophenyl)-4-(4-nitrophenyl)-Δ²-pyrazoline. Melting point 280° C 1-(4-cyanophenylcarbamoyl)-3-(4-dimethylaminophenyl)-4-(4-chlorophenyl)-Δ²-pyrazoline. Melting point 230° C 1-(4-iodophenylcarbamoyl)-3-(4-chlorophenyl)-4-phenyl-Δ²-pyrazoline. Melting point 167°-169° C 1-(4-chlorophenylcarbamoyl)-3-(4-chlorophenyl)-4-(4-nitrophenyl)-Δ²-pyrazoline. Melting point 200° C (very active compound)

1-(4-chlorophenylcarbamoyl)-3-(4-methoxyphenyl)-4-(4-nitrophenyl)-Δ²-pyrazoline. Melting point 198° C 1-(4-tert.butylphenylcarbamoyl)-3-(4-methoxyphenyl)-4-(4-nitrophenyl)-Δ²-pyrazoline. Oil 1-(3-nitrophenylcarbamoyl)-3-(4-methoxyphenyl)-4-(4-nitrophenyl)-Δ²-pyrazoline. Oil 1-(4-methylphenylcarbamoyl)-3-(4-methoxyphenyl)-4-(4-nitrophenyl)-Δ²-pyrazoline. Melting point 200° C 1-(4-chlorophenylcarbamoyl)-3-(2,4-dimethylphenyl)-4-phenyl-Δ²-pyrazoline. Melting point 194°-195° C 1-(4-methoxyphenylcarbamoyl)-3-(2,4-dimethylphenyl)-4-phenyl-Δ²-pyrazoline. Melting point 125°-128° C 1-(4-methylthiophenylcarbamoyl)-3-(2,4-dimethylphenyl)-4phenyl-Δ²-pyrazoline. Melting point 116°-118° C 1-(4-chlorophenylcarbamoyl)-3-(4-chlorophenyl)-4-(4-methylphenyl)-Δ²-pyrazoline. Melting point 172°-173° C (very active compound)

1-(4-ethylphenylcarbamoyl)-3-(4-chlorophenyl)-4-(4-methylphenyl)-Δ²-pyrazoline. Melting point 143°-144° C 1-(4-acetylphenylcarbamoyl)-3-(4-chlorophenyl)-4-(4-methylphenyl)-Δ²-pyrazoline. Melting point 158°-162° C 1-(4-chlorophenylthiocarbamoyl)-3-(4-chlorophenyl)-4-(4-methylphenyl)-Δ²-pyrazoline. Melting point 162°-164° C 1-(2-fluorophenylcarbamoyl)-3-(4-chlorophenyl)-4-phenyl-Δ²-pyrazoline. Melting point 172° C 1-(4-chlorophenylcarbamoyl)-3-(4-methylthiphenyl)-4-phenyl-Δ²-pyrazoline. Melting point 162°-163° C 1-(4-isobutylphenylcarbamoyl)-3-(4-methylthiophenyl)-4-phenyl-Δ²-pyrazoline. Melting point 154°-155° C 1-(4-methoxyphenylcarbamoyl)-3-(4-methylthiophenyl)-4-phenyl-Δ²-pyrazoline. Melting point 144°-146° C 1-(3-chloro-4-methylphenylcarbamoyl)-3-(4-methylthiophenyl)-4-phenyl-$\Delta^2$-pyrazoline. Melting point 163°-164° C 1-(4-chlorophenylcarbamoyl)-3-(4-methylsulfonylphenyl)-4-phenyl-$\Delta^2$-pyrazoline. Melting point 234° C 1-(4-chlorophenylcarbamoyl)-3-(4-nitrophenyl)-4-phenyl-$\Delta^2$-pyrazoline. Melting point 201° C 1-(4-nitrophenylcarbamoyl)-3-(4-nitrophenyl)-4-phenyl-$\Delta^2$-pyrazoline. Melting point 206° C 1-(4-isopropylphenylcarbamoyl)-3-(4-nitrophenyl)-4-phenyl-$\Delta^2$-pyrazoline. Melting point 213° C 1-(3,4-dichlorophenylcarbamoyl)-3-(4-nitrophenyl)-4-phenyl-$\Delta^2$-pyrazoline. Melting point 193° C 1-phenylcarbamoyl-3-(4-nitrophenyl)-4-phenyl-$\Delta^2$-pyrazoline. Melting point 198° C 1-[N-(4-chlorophenyl)-N-n.propylcarbamoyl]-3-(4-chlorophenyl)-4-phenyl-$\Delta^2$-pyrazoline. Melting point 111°-113° C (very active compound)

1-(4-chlorophenylcarbamoyl)-3-(4-fluorophenyl)-4-phenyl-$\Delta^2$-pyrazoline. Melting point 156°-158° C (act.comp.)

1-(4-cyano-phenylcarbamoyl)-3-(4-fluorophenyl)-4-phenyl-$\Delta^2$-pyrazoline. Melting point 213° C (very act.comp.)

1-phenylcarbamoyl-3-(4-fluorophenyl)-4-phenyl-$\Delta^2$-pyrazoline. Melting point 160°-161° C 1-(4-nitrophenylcarbamoyl)-3-(4-fluorophenyl)-4-phenyl-$\Delta^2$-pyrazoline. Melting point 238°-240° C 1-(4-ethylphenylcarbamoyl)-3-(4-fluorophenyl)-4-phenyl-$\Delta^2$-pyrazoline. Melting point 159°-168° C 1-(4-methoxyphenylcarbamoyl)-3-(4-fluorophenyl)-4-phenyl-$\Delta^2$-pyrazoline. Melting point 134° C 1-(4-n.octylphenylcarbamoyl)-3-(4-chlorophenyl)-4-phenyl-$\Delta^2$-pyrazoline. Melting point 134°-135° C 1-(4-chlorophenylcarbamoyl)-3-(3,4-methylenedioxyphenyl)-4-phenyl-$\Delta^2$-pyrazoline. Melting point 206° C 1-(4-n.octylphenylcarbamoyl)-3-(4-fluorophenyl)-4-phenyl-$\Delta^2$-pyrazoline. Melting point 123°-124° C 1-(4-fluorophenylcarbamoyl)-3-(4-fluorophenyl)-4-phenyl-$\Delta^2$-pyrazoline. Melting point 161°-162° C 1-(4-isopropoxyphenylcarbamoyl)-3-(4-fluorophenyl)-4-phenyl-$\Delta^2$-pyrazoline. Melting point 166°-167° C 1-(4-methoxyphenylcarbamoyl)-3-($\alpha$-thienyl)-4-phenyl-$\Delta^2$-pyrazoline. Melting point 164°-167° C 1-(4-methoxyphenylcarbamoyl)-3-(5-chloro-2-thienyl)-4-phenyl-$\Delta^2$-pyrazoline. Melting point 139°-141° C 1-(4-n.propylphenylcarbamoyl)-3-($\alpha$-thienyl)-4-phenyl-$\Delta^2$-pyrazoline. Melting point 148°-150° C 1-(4-chlorophenylcarbamoyl)-3-(5-chloro-2-thienyl)-4-phenyl-$\Delta^2$-pyrazoline. Melting point 145°-147° C 1-cyclohexylcarbamoyl-3-(5-chloro-2-thienyl)-4-phenyl-$\Delta^2$-pyrazoline. Melting point 117°-118° C 1-(4-isobutylphenylcarbamoyl)-3-(5-chloro-2-thienyl)-4-phenyl-$\Delta^2$-pyrazoline. Melting point 145°-146° C 1-(4-cyanophenylcarbamoyl)-3-(5-chloro-2-thienyl)-4-phenyl-$\Delta^2$-pyrazoline. Melting point 170°-173° C 1-n.undecylcarbamoyl-3-(4-chlorophenyl)-4-(4-chlorophenyl)-$\Delta^2$-pyrazoline. Oil 1-tert.butylcarbamoyl-3-(4-chlorophenyl)-4-(4-chlorophenyl)-$\Delta^2$-pyrazoline. Melting point 145° C 1-N,N-dimethylcarbamoyl-3-(4-chlorophenyl)-4-(4-chlorophenyl)-$\Delta^2$-pyrazoline. Oil 1-cyclohexylcarbamoyl-3-(2,4-dimethylphenyl)-4-phenyl-$\Delta^2$-pyrazoline. Melting point 172° C 1-cyclohexylcarbamoyl-3-(4-methylthiophenyl)-4-phenyl-$\Delta^2$-pyrazoline. Melting point 155°-158° C 1-(4-isopropylphenylcarbamoyl)-3-methyl-4-phenyl-$\Delta^2$-pyrazoline. Oil 1-(4-methoxyphenylcarbamoyl)-3-methyl-4-phenyl-$\Delta^2$-pyrazoline. Melting point 131° C 1-(3-trifluoromethylphenylcarbamoyl)-3-methyl-4-phenyl-$\Delta^2$-pyrazoline. Melting point 95° C 1-[(3,5-bis-trifluoromethyl)-phenylcarbamoyl]-3-(4-chlorophenyl)-4-n.butyl-$\Delta^2$-pyrazoline. Melting point 196°-198° C 1-(4-isobutylphenylcarbamoyl)-3-(3,4-methylenedioxyphenyl)-4-phenyl-$\Delta^2$-pyrazoline. Melting point 152° C 1-(4-methoxyphenylcarbamoyl)-3-(3,4-methylenedioxyphenyl)-4-phenyl-$\Delta^2$-pyrazoline. Melting point 154° C 1-(4-chlorophenylcarbamoyl)-3-[4-(4-bromophenyl)-phenyl]-4-phenyl-$\Delta^2$-pyrazoline. Melting point 214° C 1-(4-chlorophenylcarbamoyl)-3-phenyl-4-(4-methoxyphenyl)-$\Delta^2$-pyrazoline. Melting point 154° C 1-(4-methylphenylcarbamoyl)-3-(4-isopropoxyphenyl)-4-phenyl-$\Delta^2$-pyrazoline. Melting point 121° C.

1-(2,4-dichlorophenylcarbamoyl)-3-(4-isopropoxyphenyl)-4-phenyl-$\Delta^2$-pyrazoline. Melting point 173° C.

1-(3-trifluoromethylphenylcarbamoyl)-3-(4-isopropoxyphenyl)-4-phenyl-$\Delta^2$-pyrazoline. Melting point 181° C.

1-(4-ethylsulphonylphenylcarbamoyl)-3-(4-isopropoxyphenyl)-4-phenyl-$\Delta^2$-pyrazoline. Melting point 156° C.

1-(4-isopropoxyphenylcarbamoyl)-3-(4-isopropoxyphenyl)-4-phenyl-$\Delta^2$-pyrazoline. Melting point 141° C.

Because of their strong insecticidal activity, the substances according to the invention may be used in small dosages in controlling insects. The dosage employed depends on a variety of factors, for example, the nature of the substance used, the kind of insect, the formulation used, the condition of the vegetation infected with insects and the weather conditions. In general it holds that for controlling insects in agriculture and horticulture a dosage corresponding to 0.05 - 1 kg of the active substance per hectare will yield good results.

For practical application, the compounds according to the invention are compounded to form compositions. In these compositions the active substance is mixed with solid carrier material or dissolved or dispersed in liquid carrier material, possibly in combination with auxiliary substances, such as surface-active substances and stabilizers.

Examples of compositions according to the invention are aqueous solutions and dispersions, oil solutions and oil dispersions, pastes, dusting powders, wettable powders, miscible oils, granules, invert emulsions, aerosol compositions and fumigating candles.

Wettable powders, pastes and miscible oils are compositions in concentrate form which are diluted with water prior to or during use.

The invert emulsions are mainly used upon air application, namely when large surface areas are treated with a comparatively small quantity of composition. The invert emulsion can be prepared shortly prior to or even during spraying in the spraying apparatus by emulsifying water in an oily solution or an oily dispersion of the active substance. A few composition forms will be described in greater detail hereinafter by way of example.

Granular compositions are prepared, for example, by taking up the active substances in a solvent and impregnating the resulting solution, if desired in the presence of a binder, on granular carrier material, for example, porous granules (for example, pumice and attaclay) mineral non-porous granules (sand or ground marl), organic granules (for example, dried coffee grounds and cut tabacco stalks).

A granular composition may also be prepared by compressing the active substance together with powdered minerals in the presence of lubricants and binders, and disintegrating the compressed product to the desired grain size and sieving it.

Dusting powders can be obtained by intimately mixing the active substance with an inert solid carrier material, for example, in a concentration of 1 to 50% by weight. As examples of suitable solid carrier materials may be mentioned talcum, kaolin, pipeclay, diatomaceous earth, dolomite, gypsum, chalk, bentonite, attapulgite and colloidal $SiO_2$ or mixtures of these and similar substances. Organic carrier materials, for example, ground shells of walnuts may also be used.

Wettable powders are prepared by mixing 10 to 80 parts by weight of a solid inert carrier, for example, the above-mentioned carrier materials, with 10 to 80 parts by weight of the active substance, 1 to 5 parts by weight of a dispersion agent, for example, the lignine sulphonates or alkylnaphthalenesulphonates known for this purpose, and preferably also with 0.5 to 5 parts by weight of a wetting agent, for example, fatty alcohol sulphates, alkylarylsulphonates or fatty acid condensation products.

For the preparation of miscible oils the active compound is dissolved or finely divided in a suitable solvent which preferably is poorly miscible with water and an emulsifier is added to said solution. Suitable solvents are, for example, xylene, toluene, petroleum distillates which are rich in aromates, for example, solvent naphta, distilled tar oil and mixtures of said liquids. As emulsifiers there may be used, for example, alkylphenoxypolyglycol ethers, polyoxyethylene sorbitan esters of fatty acids or polyoxyethylene sorbitol esters of fatty acids. The concentration of the active compound in these miscible oils is not restricted to narrow limits and may vary, for example, between 2 and 50% by weight. In addition to a miscible oil there may also be mentioned as a liquid and highly concentrated primary composition a solution of the active substance in a readily water-miscible liquid, for example, acetone, to which solution a dispersion agent and possibly a wetting agent is added. Upon diluting with water shortly before or during spraying, an aqueous dispersion of the active substance is obtained.

An aerosol composition according to the invention is obtained in the usual manner by incorporating the active substance, if desired in a solvent, in a volatile liquid to be used as a propellant, for example, a mixture of chlorine-fluorine derivatives of methane and ethane.

Fumigating candles or fumigating powders, that is compositions which can generate a pesticidal smoke while burning, are obtained by taking up the active substance in a combustible mixture which, for example, may comprise as a fuel a sugar or a wood, preferably in a ground form, a substance to maintain combustion, for example, ammonium nitrate or potassium chlorate, and furthermore a substance to delay the combustion, for example, kaolin, bentonite and/or colloidal silicic acid.

In addition to the above-mentioned ingredients, the agents according to the invention may also comprise other substances known for the application of this type of agents.

For example, a lubricant, such as calcium stearate or magnesium stearate, may be added to a wettable powder or a mixture to be granulated. "Adhesives", for example, polyvinyl alcohol cellulose derivatives or other colloidal materials, such as casein, may also be added for example, so as to improve the adhesion of the pesticide to the surface to be protected.

Pesticidal compounds known per se may also be incorporated in the compositions according to the invention. As a result of this the activity spectrum of the composition is widened and synergism may occur.

For use in such combination compositions are to be considered the following known insecticidal, fungicidal and acaricidal compounds.

Insecticides, for example:

1. Chlorinated hydrocarbons, for example, 2,2-bis(p-chlorophenyl)-1,1,1-trichloroethane and hexachloro-epoxyoctahydro-dimethanonaphtalene;
2. carbamates, for example, N-methyl-1-naphtyl-carbamate;
3. dinitrophenols, for example, 2-methyl-4,6-dinitrophenol and 2-(2-butyl -4,6-dinitrophenyl)-3,3-dimethylacrylate;
4. organic phosphorus compounds, for example, dimethyl-2-methoxycarbonyl-1-methylphenylphosphate; O,O-diethyl-O-p.nitrophenylphosphorthioate; N-monomethylamide of O,O-dimethyldithiophosphoryl acetic acid;

Acaricides, for example:

5. diphenylsulphides, for example, p-chlorobenzyl p-chlorophenylsulphide and 2,4,4',5-tetrachlorodiphenylsulfide;
6. diphenylsulphonates, for example, p-chlorophenyl benzene sulphonate;
7. methyl carbinols, for example, 4,4-dichloro-a-trichloromethylbenzhydrol;
8. quinoxaline compounds, for example, methylquinoxaline dithiocarbonate.

Fungicides, for example:

9. Organic mercury compounds, for example, phenylmercury acetate and methyl mercury cyanoguanidine;
10. organic tin compounds, for example, triphenyltinhydroxide and triphenyltinacetate;
11. alkylenebisdithiocarbamates, for example, zincethylene-bisdiethiocarbamate and manganese ethylenebisdithiocarbamate;
12. and furthermore 2,4-dinitro-6-(2-octylphenylcrotonate), 1-bis(dimethylamino)phosphoryl-3-phenyl-5-amino-1,2,4-triazol, 6-methyl-quinoxaline-2,3-dithiocarbonate, 1,4-dithio antraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulphonyldiamide and tetrachloroisophthalonitrile.

As already noted above, the active compounds according to the present invention are new substances which can be prepared according to methods which are known per se for the synthesis of similar substances or are analogous thereto.

For example, the substances can be prepared by reacting a compound of formula

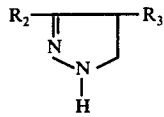

wherein $R_2$ and $R_3$ have the above indicated meanings, with a compound of formula

wherein $R_1$ and X have the meanings stated above.

The reaction is carried out at room temperature and the presence of a solvent, for example, an ether, for example, diethyl ether or petroleum ether. The compounds in which $R_4$ has the meaning of alkyl can be prepared from the pyrazolines thus obtained by alkylation in a manner known per se, for example by reaction of the compounds with $R_4 = H$ with an alkyl halide in a polar solvent under the influence of an acid binding reagent. An alternative method for preparing these compounds is the reaction of the pyrazoline unsubstituted in the 1-position with an $R_1$, $R_4$-disubstituted carbamoyl chloride or carbamic acid ester.

The above-described starting material of formula

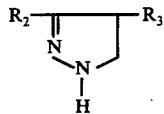

can be prepared in various manners dependent on the quality of the substituents $R_2$ and $R_3$.

If the substituents $R_2$ and $R_3$ represent a substituted or non-substituted pyridyl group, thienyl group or phenyl group, the said starting material may be prepared by reacting a compound of formula

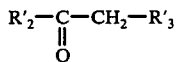

wherein $R'_2$ and $R'_3$ represent a substituted or non-substituted pyridyl group, thienyl group, or phenyl group, with formaldehyde in acid medium and in the presence of a solvent and a catalyst, a compund of formula

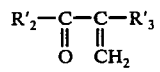

being formed.

The reaction is carried out at elevated temperature, for example, the boiling point of the solvent used. Suitable solvents are, for example, alcohols, for example methanol. A useful catalyst is, for example, piperidine.

The resulting product is then reacted with hydrazine in the presence of a solvent, for example an alcohol, for example propanol, a compound of formula

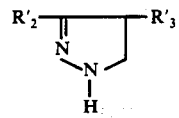

being obtained. The reaction is carried out at an elevated temperature, for example, the boiling point of the solvent used.

Starting material of the formula

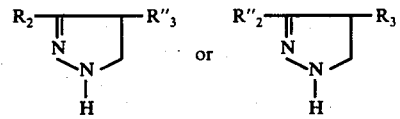

wherein $R_2$ and $R_3$ have the above-mentioned meanings and $R''_3$ and $R''_2$ represent an alkyl group or a cycloalkyl group, can be obtained by reacting a compound of formula

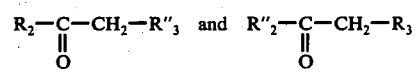

respectively, with dimethylamine and paraformaldehyde, a compound of the formula

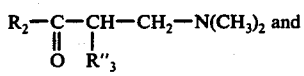

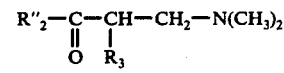

respectively, being formed. The reaction is carried out in the presence of a solvent, for example ethanol, and at elevated temperature.

The resulting products are then reacted with hydrazine at elevated temperature and in the presence of a solvent, for example ethanol, a compound of formula

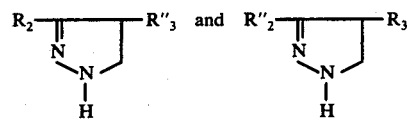

respectively, being obtained.

The invention will be described in greater detail with reference to the following examples.

EXAMPLES

1. Preparation of 1-(4-chlorophenylcarbamoyl)-3-(4-chlorophenyl)-4-phenyl-$\Delta^2$-pyrazoline and the N-methyl derivative thereof.

a. preparation of 2-phenyl-4'-chloroacrylophenone according to the reaction equation

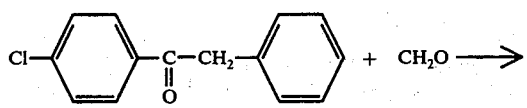

-continued

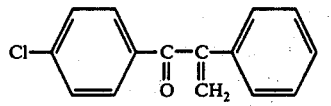

415 g of (4-chlorophenyl)-benzylketone are dissolved in 4.5 l of boiling methanol and successively added to said solution are 20 ml of piperidine, 20 ml of acetic acid and 543 ml of a 37% formaline solution. The mixture is refluxed for 3 hours, then concentrated to a volume of 2.5 l and cooled. After the addition of ice water the precipitate is sucked off and dried. Yield 427 g of 2-phenyl-4′-chloroacrylophenone of melting point 42° C.

b. preparation of 3-(4-chlorophenyl)-4-phenyl-Δ²-pyrazoline according to the reaction equation

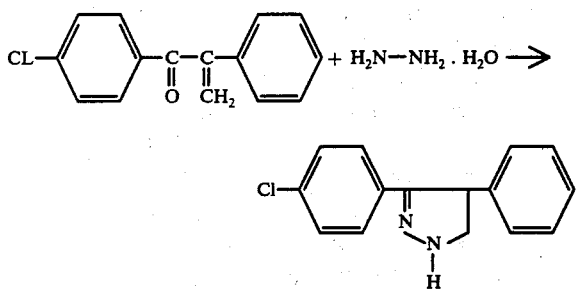

121 g of 2-phenyl-4′-chloroacrylophenone are suspended in a mixture of 280 ml of propanol and 50 ml of hydrazine hydrate. The mixture is refluxed for 3 hours after which the propanol and the excessive hydrazine are distilled off in a nitrogen atmosphere and while stirring. The residue is taken up in 200 ml of icy cold ethanol. The precipitate is separated off and then washed with ethanol and ether. Yield 97 g of 3-(4-chlorophenyl)-4-phenyl Δ²-pyrazoline of melting point 162° C.

c. preparation of 1-(4-chlorophenylcarbamoyl)-3-(4-chlorophenyl)-4-phenyl-Δ²-pyrazoline according to the reaction equation

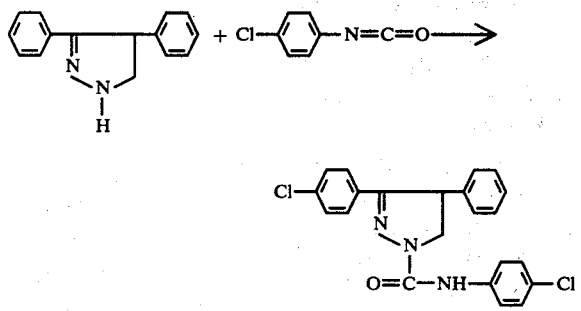

19.1 g of 3-(4-chlorophenyl)-4-phenyl-Δ²-pyrazoline are suspended in 300 ml of ether after which 11.4 g of p-chlorophenylisocyanate are added while stirring. The assembly is stirred for another 3 hours and the precipitate is sucked off. Yield 25.4 g of 1-(4-chlorophenylcarbamoyl)-3-(4-chlorophenyl)-4-phenyl-Δ²-pyrazoline of melting point 175°–177° C.

d. preparation of 1-[N-(4-chlorophenyl)-N-methyl]-carbamoyl-3-(4-chlorophenyl)-4-phenyl-Δ²-pyrazoline according to the reaction equation

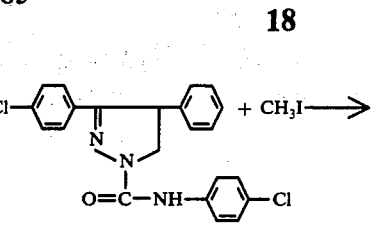

4.1 g of 1-(4-chlorophenylcarbamoyl)-3-(4-chlorophenyl)-4-phenyl-Δ²-pyrazoline are dissolved in 25 ml of dimethyl formamide. 0.72 g of KOH-power succeeded by 1.42 g of methyl iodide are added while stirring. After stirring for 30 minutes, ice water is added and sucked off. The resulting product is crystallized from methanol. Yield 3.1 g of 1-[N-(4-chlorophenyl)-N-methyl]-carbamoyl-3-(4-chlorophenyl)-4-phenyl-Δ²-pyrazoline. Melting point 142°–144° C.

The above-mentioned compounds which correspond to formula

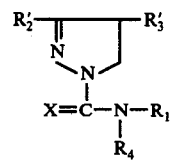

wherein $R_1$, $R'_2$, $R'_3$, $R_4$ and X have the above-mentioned meanings have been synthesized in a manner quite analogous to the above-described method of preparation. The melting points of the compounds thus prepared are stated in the list of active substances described above; if no melting points are stated, the compounds were isolated as oils.

2. Preparation of 1-(4-chlorophenyl-carbamoyl)-3-(4-chlorophenyl)-4-methyl-Δ²-pyrazoline.

a. preparation of 3-dimethylamino-2-methyl-4′-chloropropiophenone according to the reaction equation

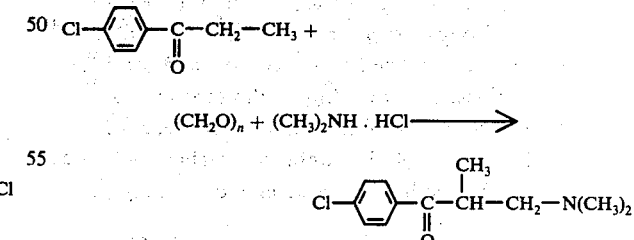

84.3 g of p-chloropropiophenone are dissolved in 50 ml of absolute ethanol and added to said solution are then 53 g of dimethylamine HCl and 20 g of paraformaldehyde. The assembly is refluxed for 20 hours, then cooled, diluted with water and extracted with petroleum ether. The aqueous layer is treated with lye until a basic reaction and the reaction product is extracted with ether. The extracts are evaporated and the resulting product, an oil, is used for the next reaction step.

b. preparation of 3-(4-chlorophenyl)-4-methyl-$\Delta^2$-pyrazoline according to the reaction equation

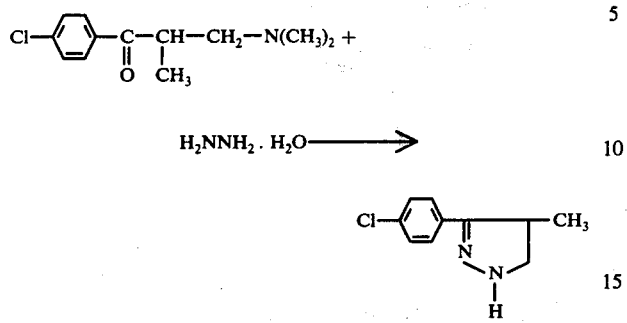

11.3 g of 3-dimethylamino-2-methyl-4'-chloropropiophenone as obtained sub(a) are dissolved in 20 ml of ethanol after which 3 ml of hydrazine hydrate are added. After refluxing the whole for 2 hours it is evaporated to dryness in vacuo. Yield 9.7 g of crystalline 3-(4-chlorophenyl)-4-methyl-$\Delta^2$-pyrazoline of melting point 80° C.

c. preparation of 1-(4-chlorophenylcarbamoyl)-3-(4-chlorophenyl)-4-$\Delta^2$-pyrazoline according to the reaction equation

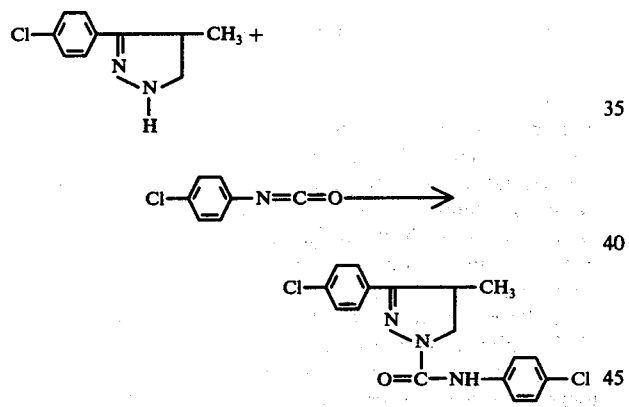

2 g of 3-(4-chlorophenyl)-4-methyl-$\Delta^2$-pyrazoline are dissolved in 15 ml of ether after which 1.55 g of p-chlorophenylisocyanate are added while stirring. After leaving the resulting bright solution to stand for a few hours, crystallisation set in. After 2 days the crystals are sucked off and recrystallized from petroleum ether. Yield 2.4 g of 1-(4-chlorophenyl carbamoyl)-3-(4-chlorophenyl)-4-methyl $\Delta^2$-pyrazoline of melting point 139° C.

The above-mentioned substances which correspond to the formula

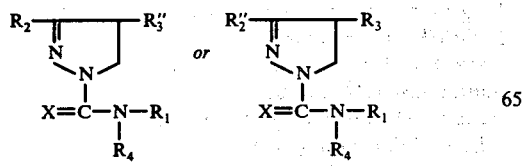

wherein $R_1$, $R_2$, $R_3$, $R_4$, $R''_3$ and X have the above-mentioned meanings have been prepared in a manner quite analogous to that described above. The melting points of the resulting substances are stated in the aforementioned list of active substances.

TEST RESULTS

1) Biological methods

The insecticidal evaluations were usually performed with suspensions made by pouring out quantities of a 10,000-ppm acetonic stock solution into water, with stirring.

Compounds insufficiently soluble in acetone were thoroughly milled in a laboratory glass mill.

The several species were tested as follows:

a) *Aedes aegypti L.* (yellow Fever mosquito)

Aliquots of 100 ml of tap water containing 1, 0,3, 0,1, 0,03, etc., ppm respectively, of the 1,3,4-substituted pyrazolines, were supplied with ten 1-day old larvae and kept at 25° C. The larvae were fed with malt yeast powder. After 14 days, when the pupae of the untreated insects had hatched, the mortality percentages were calculated with a correction for the natural mortality according to Abott. There were three replicates per treatment.

b) *Pieris brassicae L.* (Large Cabbage White).

Potted cabbage seedlings were sprayed with a suspension of the toxicant until runoff.

The suspensions contained 300, 100, 30, 10, 3, etc., ppm respectively of the compound. When dry, the plants were placed in plastic cylinders provided with five third-instar caterpillars and kept under a day: night circle of 18 : 6 hr and a temperature and relative humidity of 24° C., 60 – 70% and 19° C., 80 – 90% respectively.

There were three replicates per treatment. After 6 days the mortality percentages were calculated according to Abbott's formula. (Abbott, W. S., J.Econ. Entomol. 18, 265 (1925).

c) *Lepinotassa decemlineata Say* (Colorado Potato Beetle)

Potato shoots, placed in flasks containing tap water, were sprayed with a suspension of the compound until runoff. The concentrations of the suspensions were 300, 100, 30, 10, 3 etc., ppm, respectively. Upon drying, the shoots were placed in plastic cylinders and provided with ten third-instar larvae. After this the procedure and the environmental circumstances were identical with those applied to the Large Cabbage White.

2) Results:

The results of the tests are given in the following table; + means 90 - 100% mortality, ± means 50 - 89% mortality and — means 0 - 49% mortality. The first sign is for the highest concentration, the other for the dilutions as mentioned above.

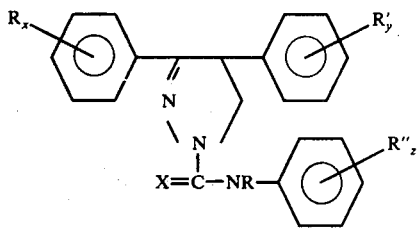

| $R_x$ | $R_y'$ | $R_z''$ | Cola L 300 ppm | Pieris 300 | Aedes 1 | Remarks | |
|---|---|---|---|---|---|---|---|
| 4-Cl | 4-Cl | 4-Cl | +++++++± - | +++++++- | ++++- | R = H | X |
| H | H | 4-OCH₃ | +++++- | ±- | ++- | " | |
| H | H | 4-C(CH₃)₃ | ++++±- | +++++±- | - | " | |
| H | H | 4-n-C₄H₉ | +++++- | +++- | - | " | |
| H | H | 4-C₂H₅ | +++++±- | ++- | +++- | " | |
| H | H | H | ++++±- | - | - | " | |
| H | H | 4-Br | +++++++±- | +++±- | +++±- | " | |
| H | H | 4-Cl | +++++++±- | +++±- | +++- | " | |
| H | H | 4-NO₂ | ++++++- | ++- | - | " | |
| 4-Cl | H | H | +++++±- | ++- | - | " | |
| 4-Cl | H | 4-Cl | +++++++±- | +++++±- | +++±- | " | |
| 4-Cl | 4-Cl | 4-OCH₃ | +++++++- | ++++±- | +++- | " | |
| 4-Cl | 4-Cl | 4-SCH₃ | ++++++±±- | +++++- | ++++- | " | |
| 4-Cl | 4-Cl | 4-C(CH₃)₃ | +++++±- | ++++±- | - | " | |
| 4-Cl | 4-Cl | 4-φ | +++++- | +±- | - | " | |
| 4-Cl | 4-Cl | 4-CH₃ | ++++++±- | +++±- | ±- | " | |
| 4-Cl | 4-Cl | H | +++++±- | ++±- | +- | " | |
| 4-Cl | 4-Cl | 4-I | +++++++±- | ++++++±- | ++- | " | |
| 4-Cl | 4-Cl | 4-Br | ++++++±±± - | ++++++±- | +++++- | " | |
| 4-Cl | 4-Cl | 4-F | +++++++±- | ++++++- | ++++- | " | |
| 4-Cl | 4-Cl | 3-Cl | ++++++±- | ++++- | +++- | " | |
| 4-Cl | 4-Cl | 3-CF₃ | ++++++- | ++++±- | ++++- | " | |
| 4-Cl | 4-Cl | 3,4-Cl₂ | +++++±- | +++++- | +- | " | |
| 4-Cl | 4-Cl | 4-NO₂ | ++++++±- | ++++++- | ++++- | " | |
| 4-Cl | 4-Cl | 3-NO₂ | ++++++- | ++++- | +++±- | " | |
| H | 4-Cl | 4-OCH₃ | ++++++±- | +±- | +++±- | " | |
| H | 4-Cl | 4-C₂H₅ | +++++±±- | +++- | +++±- | " | |
| H | 4-Cl | 4-Cl | +++++++±- | ++++- | ++++- | " | |
| H | 4-Cl | 3,4-Cl₂ | ++++++++±- | +++++- | +++- | " | |
| 4-Cl | 2,4-Cl₂ | 4-Cl | ++++++±- | ++++- | +++- | " | |
| 4-Cl | 2,4-Cl₂ | 4-F | ++++±±- | ++++±- | ++- | " | |
| 4-Cl | 2,4-Cl₂ | 3,4-Cl₂ | ++++++- | ++- | - | " | |
| H | H | H | +++±- | - | - | " | X |
| 4-Cl | 4-Cl | H | +++++±- | +±- | - | " | |
| 4-Cl | H | 4-Cl | ++++++- | ++++- | ++++- | R = CH₃ | X |
| 4-Cl | H | 3-NO₂ | +++++±- | +++±- | - | " | |
| 4-Cl | H | 4-φ² | +++++±- | ++++±- | +++- | R = H | X |
| 4-Cl | H | 4-Br | +++++++±±- | ++++++±- | ++++± | " | X = O |
| 4-Cl | 4-Cl | 4-C—CH₃<br>‖<br>O | ++±±-- | ++++-- | ++- | " | |
| 4-Cl | 4-Cl | 4-CF₃ | ++++++++- | +++++++±- | +++++±± | " | " |
| 4-Cl | 4-Cl | 4-Cl | +++++ | ++++±±- | ±- | " | " |
| 4-Cl | H | 4-SCH₃ | +++++ | +++++±- | +++- | " | " |
| 4-Cl | H | 4-Cl | ±++ | +++ | ++- | " | " |
| 4-Cl | H | 4-CH₃ | +++±±- | +----- | ±- | " | " |
| 4-Cl | H | 4-CH₂-CH(CH₃)₂ | +++±- | +++±- | - | " | " |
| 4-Cl | H | 4-O-φ(2,6-Cl₂) | ++++-- | ++±--- | - | " | " |
| 4-CH₃ | 4-Cl | 4-Cl | ++++++±±- | +++--- | +++- | " | " |
| 4-CH₃ | 4-Cl | 4-CH(CH₃)₂ | ++++++- | ++++-- | ±- | " | " |
| 4-CH₃ | 4-Cl | 4-O-CH(CH₃)₂ | ++++++±±- | +++-- | ++++- | " | " |
| 4-CH₃ | 4-Cl | 3-CF₃ | +++++- | - | - | " | " |
| 4-CH₃ | 4-Cl | 4-n-C₃H₇ | +++++- | ++±- | ±- | " | " |
| 4-Cl | 4-Cl | 4-C₂H₅ | +++++±- | ++++- | ++++- | " | " |
| 4-Cl | 4-Cl | 3-Cl,4-CH₃ | +++++±- | +++++±- | +- | " | " |
| 4-Cl | 4-Cl | 4-SO₂-C₂H₅ | ++++±±- | ++++++±- | ++++- | " | " |
| 4-Cl | 4-Cl | 4-SO₂-CH₃ | +++++±- | +++++±- | +++++±±- | " | " |
| 4-Cl | 4-Cl | 4-O-CH(CH₃)₂ | +++++±- | +++++±- | ++++±±- | " | " |
| 4-Cl | 4-Cl | 4-N(CH₃)₂ | +++±- | +++- | +- | " | " |
| 4-Cl | 4-Cl | 3-Cl,4-OCH₃ | ++++±- | ++- | ±- | " | " |
| 4-Cl | H | 4-C(CH₃)₃ | +++++±- | ++++++- | - | " | " |
| 4-Cl | H | 4-n-C₄H₉ | +++++±- | ++++- | - | " | " |
| 4-Cl | H | 4-C₂H₅ | +++++±- | ++++±- | +++- | " | " |
| 4-Cl | H | 3-CF₃ | +++++±- | ++++±- | ±- | " | " |
| 4-Cl | H | 4-O-CH(CH₃)₂ | +++++±- | ++++±- | +++- | " | " |
| 4-Cl | H | 4-CF₃ | ++++++++± | +++++++- | +++- | " | " |
| 4-Cl | H | 3-NO₂,4-OCH₃ | +++±±- | +----- | - | " | " |
| 4-Cl | H | 4-F | ++++++- | ++++++- | ++++++-- | " | " |
| 4-Cl | H | 3,4-Cl₂ | ++++++- | ++++++- | - | " | " |
| 4-Cl | 4-Cl | 4-OC₂H₅ | ++++++- | +++++±- | ++++- | " | " |
| 4-OCH₃ | 4-Cl | 4-Cl | ++++++±- | +++-- | +++- | " | " |
| 4-OCH₃ | 4-Cl | 4-OCH(CH₃)₂ | ++++++±- | ++±-- | +++- | " | " |
| 4-OCH₃ | 4-Cl | 4-NO₂ | +++++±- | +++++±- | ++- | " | " |
| 4-Cl | H | 4-CN | +++++±- | +++++±- | +++- | " | " |
| 4-N(CH₃)₂ | 4-Cl | 4-Cl | ++++++- | +++±±- | ++++- | " | " |
| 4-N(CH₃)₂ | 4-Cl | 4-C₂H₅ | ++++++- | ++±- | +++- | " | " |
| 4-N(CH₃)₂ | 4-Cl | 4-SO₂-C₂H₅ | ++++-- | ++±-- | - | " | " |
| 4-O-CH(CH₃)₂ | H | 4-Cl | ++++++±- | +++++±- | +++- | " | " |

-continued

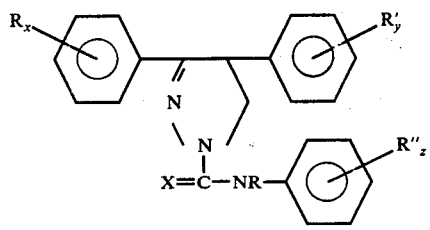

| $R_x$ | $R_y'$ | $R_z''$ | Cola L 300 ppm | Pieris 300 | Aedes 1 | Remarks | |
|---|---|---|---|---|---|---|---|
| 4-O-CH(CH$_3$)$_2$ | H | 4-C$_2$H$_5$ | ++++±− | ++++− | ++− | " | " |
| 4-O-CH(CH$_3$)$_2$ | H | 4-O-CH(CH$_3$)$_2$ | +++++++− | ++++− | +++− | " | " |
| 4-Cl | 4-Cl | 4-CN | ++++++− | +++++− | ++++− | " | " |
| 4-Cl | 4-Cl | 4-Cl | ++++++− | +++++±− | +++ | R = CH$_3$ | " |
| 4-Br | H | 4-Cl | ++++++± | ++++++− | ++++− | R = H$_3$ | " |
| 4-Br | H | 4-Br | ++++++± | ++++++− | ++++− | " | " |
| 4-Br | H | 4-O-CH(CH$_3$)$_2$ | +++++++− | ++++++− | ±++±− | " | " |
| 4-Br | H | 4-CH$_2$-CH(CH$_3$)$_2$ | ++++±− | ++±− | − | " | " |
| 4-Br | 4-Cl | 4-Cl | +++++ | +++++ | ++++− | " | " |
| 4-Br | 4-Cl | 3-CF$_3$ | +++++± | +++±− | +++− | " | " |
| 4-CH$_3$ | H | 4-Cl | ++++++± | +− | +++− | " | " |
| 4-CH$_3$ | H | 4-CH$_3$ | +++++±− | +− | − | " | " |
| 4-CH$_3$ | H | 4-C$_3$H$_7$ | +++++±− | ++±− | +− | " | " |
| 4-CH$_3$ | H | 4-OCH$_3$ | ++++++± | +− | +− | " | " |
| 4-Cl | 4-Cl | 4-Cl | +++++ | +++++ | − | " | " |
| 4-N(CH$_3$)$_2$ | 4-Cl | 4-CN | ++++± | ++±− | +++− | " | " |
| 4-Cl | H | 4-I | +++++ | ++++ | ++++− | " | " |
| 4-Cl | 4-No$_2$ | 4-Cl | +++++++− | +++++++ | ++++±− | " | " |
| 4-Cl | H | 4-Cl | +++++++±− | +++++±− | ++++− | R" = C$_2$H$_5$ | " |
| 4-Cl | H | 4-Cl | +++++±− | +++++− | +++− | R = C$_8$H$_{17}$(h) | " |
| 4-Cl | H | 4-Cl | +++++±− | ++++±±− | +++− | R = C$_4$H$_9$(n) | " |

What is claimed is:

1. A compound of the formula

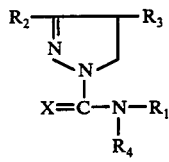

wherein R$_1$ is a member selected from the group consisting of alkyl of 1 to 4 carbon atoms, cycloalkyl of 3 to 6 carbon atoms, phenylalkyl, ring halogenated phenylalkyl, ring nitrated phenylalkyl, ring alkylated phenylalkyl, phenyl, phenyl substituted in the 2, 3 or 4 positions with up to two substituents selected from the group consisting of halogen, alkyl of 1 to 4 carbon atoms, halogenated alkyl of 1 to 4 carbon atoms, cycloalkyl of 3 to 6 carbon atoms, alkylthio of 1 to 4 carbon atoms, alkoxy of 1 to 4 carbon atoms, dialkylamino wherein each alkyl radical is of 1 to 4 carbon atoms, alkylsulphonyl of 1 to 4 carbon atoms, acyl of an aliphatic monocarboxylic acid, acylamino wherein the acyl moiety is of an aliphatic monocarboxylic acid, cyano, nitro, phenyl and halogenated phenyl, R$_2$ and R$_3$ are each independently selected from the group consisting of alkyl of 1 to 4 carbon atoms, cycloalkyl of 3 to 6 carbon atoms, phenyl, phenyl substituted with up to two substituents selected from the group consisting of halogen, alkyl of 1 to 4 carbon atoms, halogenated alkyl of 1 to 4 carbon atoms, cycloalkyl of 3 to 6 carbon atoms, alkylthio of 1 to 4 carbon atoms, alkoxy of 1 to 4 carbon atoms, mono or dialkylamino wherein each alkyl is of 1 to 4 carbon atoms, nitro, phenyl, halogenated phenyl and cyano, R$_4$ is a member selected from the group consisting of hydrogen and alkyl of 1 to 15 carbon atoms and wherein X is oxygen or sulfur.

2. A compound of the formula

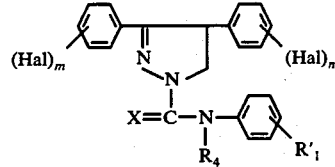

wherein Hal is halogen, R'$_1$ is hydrogen or a substituent present in the 3- or 4-position of the phenyl ring selected from the group consisting of halogen, an alkyl group of 1–4 carbon atoms, halogenated alkyl of 1–4 carbon atoms, alkylthio of 1–4 carbon atoms, alkoxy of 1–4 carbon atoms, cyano, nitro group and 3,4-dichloro, R$_4$ is a hydrogen atom or alkyl of 1-15 carbon atoms, X is oxygen or sulphur, m = 0 or 1, and n = 0, 1 or 2.

3. A compound of the formula

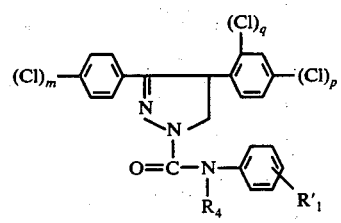

wherein R'$_1$ and R$_4$ have the meanings of claim 2, m = 0 or 1, p = 0 or 1, q = 0 or 1.

4. A compound of the formula

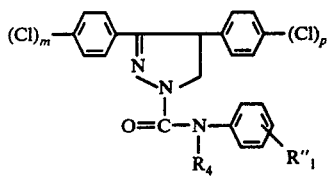

wherein R″₁ is fluorine, chlorine, bromine or iodine present in the position or in which R″ is 3,4-dichloro, R₄ has the meanings of claim 3, and $m = = 0$ or $1, p = 0$ or 1.

5. 1-(4-chlorophenyl-carbamoyl)-3-(4-chlorophenyl)-4-phenyl-Δ²-pyrazoline.

6. 1-(4-chlorophenylcarbamoyl)-3, 4-bis-(4-chlorophenyl)-Δ²-pyrazoline.

7. 1-(4-phenylcarbamoyl)-3,4-diphenyl-Δ²-pyrazoline.

8. 1-(4-chlorophenylcarbamoyl)-3,4-diphenyl-Δ²-pyrazoline.

9. 1-(4-iodophenylcarbamoyl)-3,4-bis-(4-chlorophenyl)-Δ²-pyrazoline.

10. 1-(4-fluorophenylcarbamoyl)-3,4-bis-(4-chlorophenyl)-Δ²-pyrazoline.

11. 1-(4-chlorophenylcarbamoyl)-3-phenyl-4-(4-chlorophenyl)-Δ²-pyrazoline.

12. 1-(3,4-dichlorophenylcarbamoyl)-3-phenyl-4-(4-chlorophenyl)-Δ²-pyrazoline.

13. 1-(4-methoxyphenylcarbamoyl)-3,4-bis-(4-chlorophenyl)-Δ²-pyrazoline.

14. 1-(3-nitrophenylcarbamoyl)-3,4-bis-(4-chlorophenyl)-Δ²-pyrazoline.

15. 1-[N-(4-chlorophenyl)-N-methyl]-carbamoyl-3-(4-chlorophenyl)-4-phenyl-Δ²-pyrazoline.

* * * * *